US00PP29455P3

(12) United States Plant Patent
Moss et al.

(10) Patent No.: US PP29,455 P3
(45) Date of Patent: Jul. 3, 2018

(54) ***GERANIUM* PLANT NAMED 'HEXHAM VELVET'**

(50) Latin Name: *Geranium wallichianum*
Varietal Denomination: Hexham Velvet

(71) Applicants: Robin Moss, Hexham (GB); Cyril Foster, Morpeth (GB)

(72) Inventors: Robin Moss, Hexham (GB); Cyril Foster, Morpeth (GB)

( * ) Notice: Subject to any disclaimer, the term of this patent is extended or adjusted under 35 U.S.C. 154(b) by 3 days.

(21) Appl. No.: 15/330,764

(22) Filed: Nov. 5, 2016

(65) Prior Publication Data

US 2018/0132409 P1 May 10, 2018

(51) Int. Cl.
*A01H 5/02* (2018.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — C. A. Whealy

(57) ABSTRACT

A new and distinct cultivar of *Geranium* plant named 'Hexham Velvet', characterized by its low-growing and outwardly spreading plant habit; vigorous growth habit; freely branching habit; freely flowering habit; sterile upward-facing purple violet-colored flowers with almost black-colored venation and small white-colored centers; long and continuous flowering period; and good garden performance.

3 Drawing Sheets

Botanical designation: *Geranium wallichianum.*
Cultivar denomination: 'HEXHAM VELVET'.

BACKGROUND OF THE INVENTION

The present invention relates to a new and distinct cultivar of *Geranium* plant, botanically known as *Geranium wallichianum* and hereinafter referred to by the name 'Hexham Velvet'.

The new *Geranium* plant is a product of a planned breeding program conducted by the Inventors in Rothbury, Northumberland, United Kingdom. The objective of the breeding program is to create new low-growing *Geranium* plants with numerous upward-facing flowers that are sterile.

The new *Geranium* plant originated from a cross-pollination made by the Inventors in July, 2004 in Rothbury, Northumberland, United Kingdom of *Geranium wallichianum* 'Syabru', not patented, as the female, or seed, parent with an unnamed selection of *Geranium wallichianum*, not patented, as the male, or pollen, parent. The new *Geranium* plant was discovered and selected by the Inventors as a single flowering plant within the progeny of the stated cross-pollination in a controlled environment in Rothbury, Northumberland, United Kingdom in July, 2005.

Asexual reproduction of the new *Geranium* plant by cuttings in a controlled environment in Rothbury, Northumberland, United Kingdom since the spring of 2006, has shown that the unique features of this new *Geranium* plant are stable and reproduced true to type in successive generations.

SUMMARY OF THE INVENTION

Plants of the new *Geranium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hexham Velvet'. These characteristics in combination distinguish 'Hexham Velvet' as a new and distinct *Geranium* plant:

1. Low-growing and outwardly spreading plant habit.
2. Vigorous growth habit.
3. Freely branching habit.
4. Freely flowering habit.
5. Sterile upward-facing purple violet-colored flowers with almost black-colored venation and small white-colored centers.
6. Long and continuous flowering period.
7. Good garden performance.

Plants of the new *Geranium* differ primarily from plants of the female parent, 'Syabru', in the following characteristics:

1. Plants of the new *Geranium* are shorter and lower-growing than plants of 'Syabru'.
2. Plants of the new *Geranium* and 'Syabru' differ in flower color as plants of 'Syabru' have light magenta colored-flowers.
3. Plants of the new *Geranium* have larger and flatter flowers than plants of 'Syabru'.
4. Plants of the new *Geranium* have sterile flowers whereas plants of 'Syabru' produce seeds.

Plants of the new *Geranium* differ primarily from plants of the male parent selection in the following characteristics:

1. Plants of the new *Geranium* are shorter and lower-growing than plants of the male parent selection.
2. Plants of the new *Geranium* and the male parent selection differ in flower color as plants of the male parent selection have light violet blue colored-flowers with white-colored centers.

3. Plants of the new *Geranium* have sterile flowers whereas plants of the male parent selection produce seeds.

Plants of the new *Geranium* can be compared to plants of *Geranium wallichianum* 'Rosetta', disclosed in U.S. Plant Pat. No. 19,109. In side-by-side comparisons, plants of the new *Geranium* differ primarily from plants of 'Rosetta' in the following characteristics:

1. Plants of the new *Geranium* are shorter, lower-growing and broader than plants of 'Rosetta'.
2. Plants of the new *Geranium* and 'Rosetta' differ in flower color as plants of 'Rosetta' have pink-colored flowers with light pink-colored centers.

BRIEF DESCRIPTION OF THE PHOTOGRAPHS

The accompanying colored photographs illustrate the overall appearance of the new *Geranium* plant showing the colors as true as it is reasonably possible to obtain in colored reproductions of this type. Colors in the photographs may differ slightly from the color values cited in the detailed botanical description which accurately describe the colors of the new *Geranium* plant.

The photograph on the first sheet comprises a top perspective view of typical flowering plants of 'Hexham Velvet' grown in an outdoor nursery.

The photograph on the second sheet is a close-up view of a typical flowering plant of 'Hexham Velvet'.

The photograph on the third sheet is a close-up view of the upper (right) and lower (left) surfaces of typical flowers (top) and leaves (bottom).

DETAILED BOTANICAL DESCRIPTION

The aforementioned photographs and following observations, measurements and values describe plants grown during the summer and autumn in 15-liter containers in an outdoor nursery in Bressingham Diss, Norfolk, United Kingdom. During the production of the plants, day temperatures averaged 14° C. and night temperatures averaged 9° C. Plants were three years old when the photographs and the description were taken. In the detailed description, color references are made to The Royal Horticultural Society Colour Chart, 2000 Edition, except where general terms of ordinary dictionary significance are used.

Botanical classification: *Geranium wallichianum* 'Hexham Velvet'.

Parentage:

*Female, or seed, parent.*—*Geranium wallichianum* 'Syabru', not patented.

*Male, or pollen, parent.*—Unnamed selection of *Geranium wallichianum*, not patented.

Propagation:

*Type.*—By cuttings.

*Time to initiate roots, summer.*—About ten days at temperatures about 16° to 20° C.

*Time to produce a rooted young plant, summer.*—About three months at temperatures about 16° to 20° C.

*Root description.*—Main roots are fleshy, medium in thickness and close to 177A in color; lateral roots are fibrous, fine and close to 177C in color.

*Rooting habit.*—Moderate branching; medium density.

Plant description:

*Plant and growth habit.*—Hardy herbaceous perennial; low-growing and outwardly spreading plant habit; vigorous growth habit.

*Plant height.*—About 25 cm.

*Plant width.*—About 75 cm.

*Branching habit.*—Freely branching habit with about 15 to 20 lateral branches developing per plant.

*Lateral branch length.*—About 75 cm.

*Lateral branch diameter.*—About 4 mm.

*Internode length.*—About 6 cm.

*Lateral branch aspect.*—Outwardly and horizontally spreading.

*Lateral branch strength.*—Strong.

*Lateral branch texture.*—Pubescent.

*Lateral branch color.*—Close to 136D; older stems lightly flushed with close to 176A.

Leaf description:

*Arrangement.*—Opposite, simple.

*Length.*—About 4.5 cm.

*Width.*—About 4 cm.

*Shape.*—Deeply dissected.

*Apex.*—Acute.

*Base.*—Hastate.

*Margin.*—Five palmate lobes; lobes biserrate.

*Venation pattern.*—Palmate; reticulate.

*Texture, upper and lower surfaces.*—Pubescent; rough.

*Color.*—Developing leaves, upper and lower surfaces: Close to 136C. Fully developed leaves, upper surface: Close to 136A; in the autumn, leaves are flushed with close to 176A; venation, close to 136D. Fully developed leaves, lower surface: Close to 136C; venation, close to 136C.

*Petioles.*—Length: About 5 cm. Diameter: About 3 mm. Texture, upper and lower surfaces: Pubescent. Color, upper and lower surfaces: Close to 136C.

Flower description:

*Flowering habit.*—Single rotate flowers; flowers axillary; flowers face mostly upright; freely flowering habit with about 24 flowers per plant.

*Fragrance.*—None detected.

*Flowering season.*—In The United Kingdom, flowering is continuous from June to September; plants begin flowering about 107 days after planting.

*Flower longevity.*—Individual flowers last about ten days on the plant; petals not persistent, sepals and gynoecium persistent.

*Flower buds.*—Length: About 1 cm. Diameter: About 8 mm. Shape: Elliptical. Color: Close to 136B.

*Flower diameter.*—About 4 cm.

*Flower height* (*depth*).—About 2 cm.

*Petals.*—Quantity per flower: Five in a single whorl. Length: About 2 cm. Width: About 1.5 cm. Shape: Obcordate. Apex: Retuse. Base: Acute. Margin: Entire. Texture, upper and lower surfaces: Smooth, glabrous. Color: When opening, upper and lower surfaces: Close to 80B; venation, close to 202A. Fully opened, upper and lower surfaces: Close to 81A; towards the base, close to 155D; venation, close to 202A; main color becoming closer to 81B with development.

*Sepals.*—Quantity per flower: Five, arranged in a single whorl. Length: About 1 cm. Diameter: About 5 mm. Shape: Lanceolate. Apex: Acute. Base: Cuneate. Margin: Entire. Texture, upper and lower surfaces: Smooth, glabrous. Color: When opening, upper and lower surfaces: Close to 137C. Fully opened, upper surface: Close to 137B. Fully opened, lower surface: Close to 137B lightly flushed with close to 81D.

*Peduncles*.—Length: About 4 cm. Diameter: About 2 mm. Aspect: Upright to curved. Strength: Strong. Color: Close to 136C lightly flushed with close to 81D.

*Pedicels*.—Length: About 3 cm. Diameter: About 1.5 mm. Aspect: Upright to curved. Strength: Strong. Color: Close to 136C lightly flushed with close to 81D.

*Reproductive organs*.—Androecium: Stamen quantity per flower: About ten. Anther length: About 3 mm. Anther shape: Oblong. Anther color: Close to 202A. Pollen amount: Scarce. Pollen color: Close to 197D. Gynoecium: Pistil quantity per flower: One. Pistil length: About 7 mm. Stigma shape: Reflexed. Stigma color: Close to 202A. Style length: About 4 mm. Style color: Close to 202A. Ovary color: Close to 81A.

*Seeds and fruits*.—Plants of the new *Geranium* have sterile flowers and seed and fruit development have not been observed.

Pathogen & pest resistance: Plants of the new *Geranium* have been not been observed to be resistant to pathogens and pests common to *Geranium* plants.

Garden performance: Plants of the new *Geranium* have been observed to have good garden performance; to tolerate rain, wind and high temperatures about 30° C.; and to be hardy to USDA Zone 5.

It is claimed:

1. A new and distinct *Geranium* plant named 'Hexham Velvet' as illustrated and described.

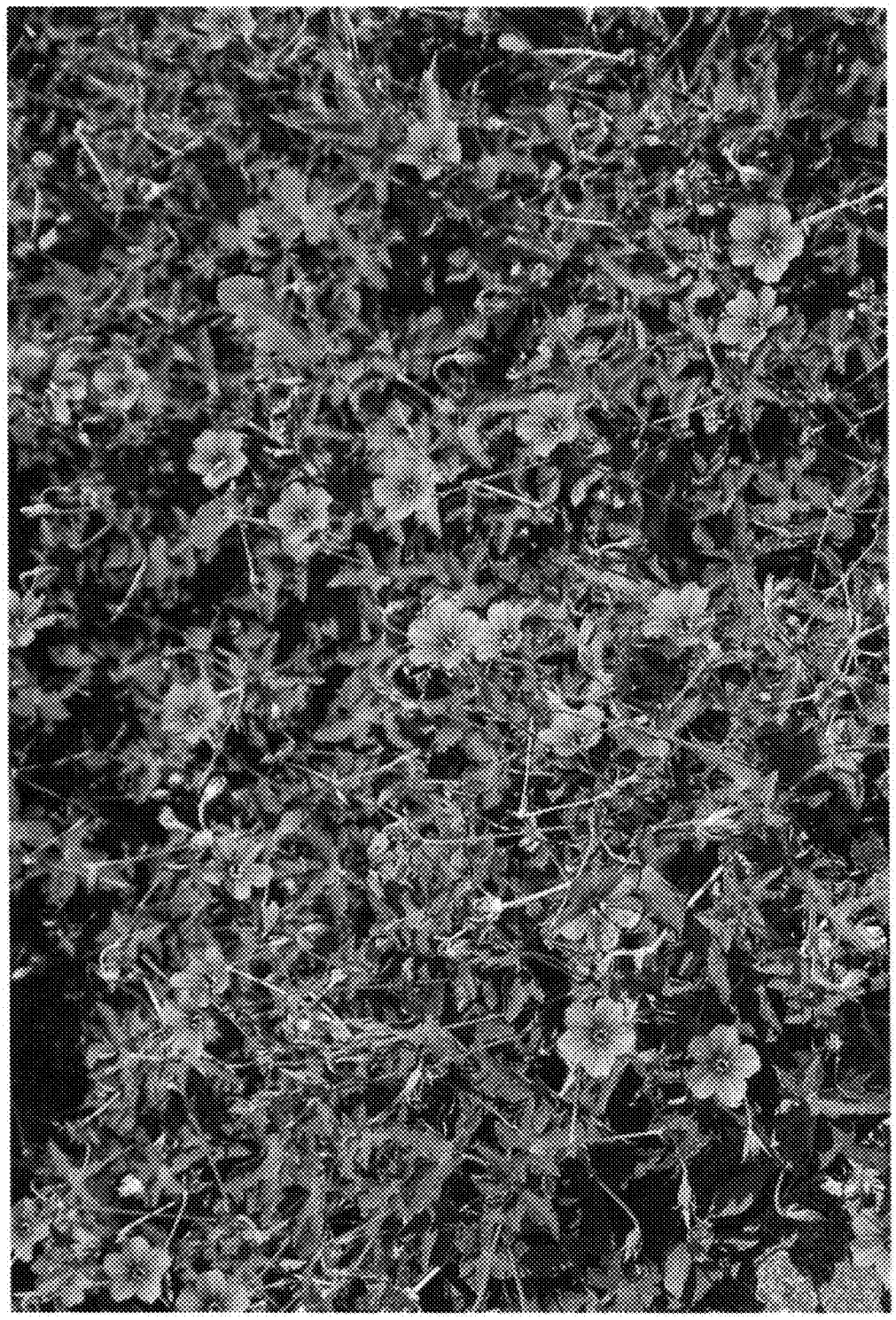

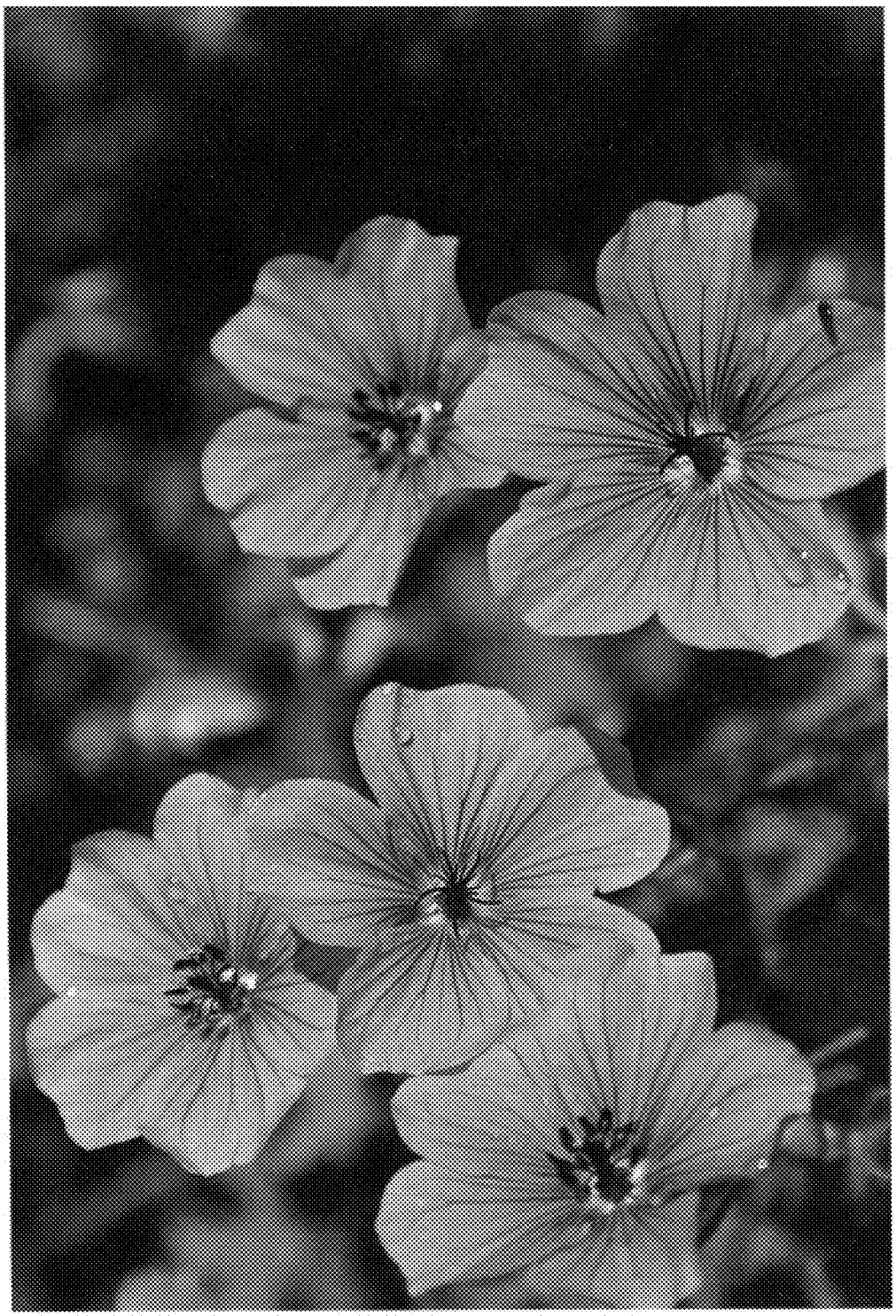

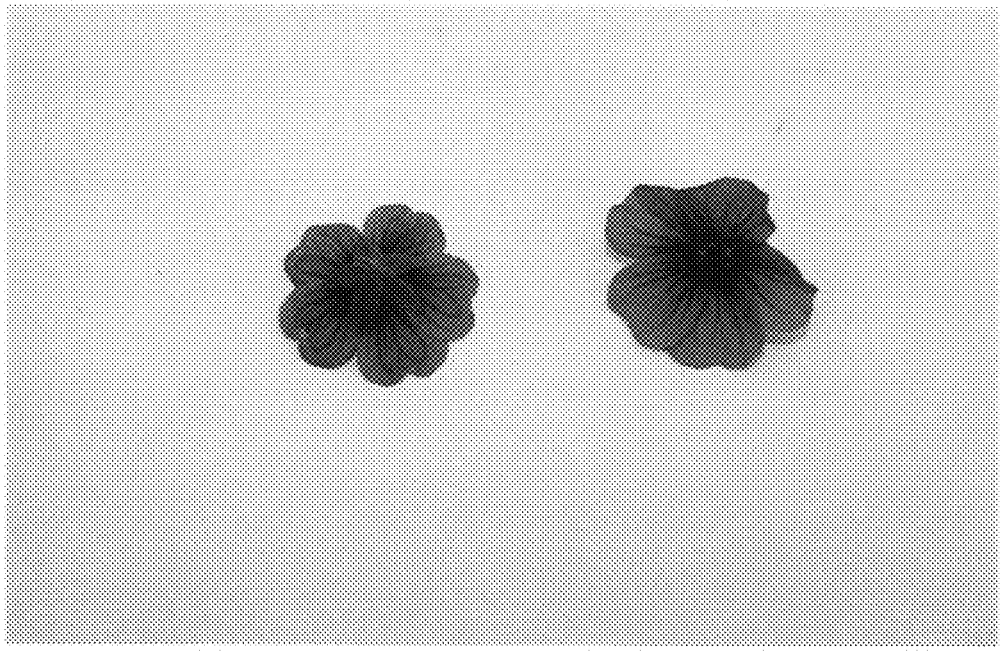
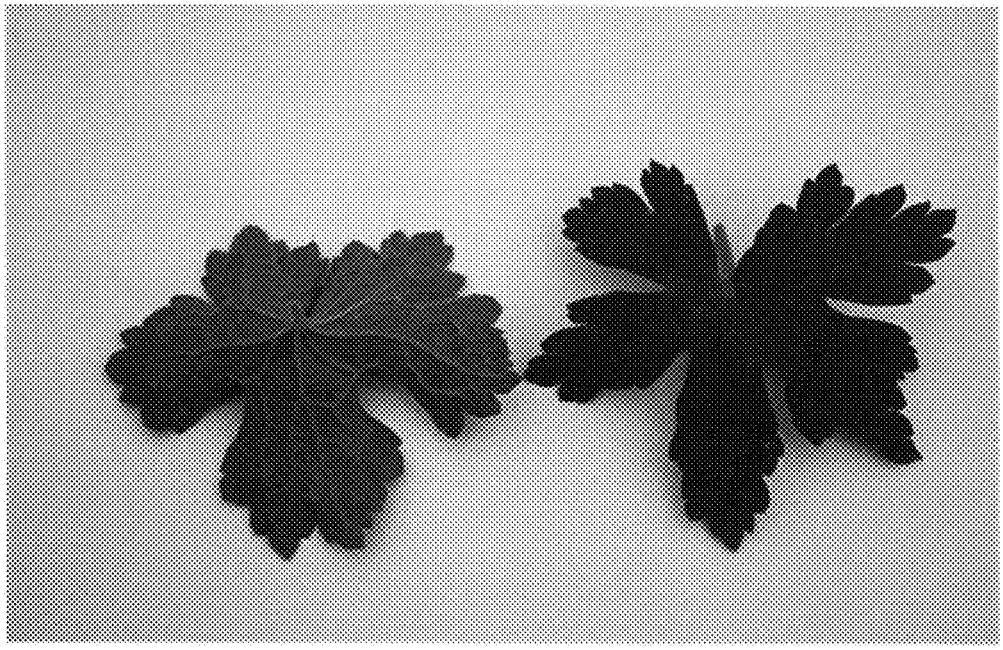

* * * * *